(12) United States Patent
Gaudoin

(10) Patent No.: US 6,561,788 B1
(45) Date of Patent: May 13, 2003

(54) MODULAR MOLD DESIGNS

(75) Inventor: Henri A. Gaudoin, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 298 days.

(21) Appl. No.: 09/585,807

(22) Filed: May 31, 2000

(51) Int. Cl.[7] ............................................. B29C 49/48
(52) U.S. Cl. ...................... 425/522; 249/102; 425/182; 425/195; 425/403; 425/470
(58) Field of Search ................................ 249/102, 160; 425/522, 470, 182, 195, 191, 403; 264/573

(56) References Cited

U.S. PATENT DOCUMENTS

| | | | |
|---|---|---|---|
| 3,837,347 A | 9/1974 | Tower | |
| 3,882,852 A | 5/1975 | Sinnreich | |
| 4,130,617 A * | 12/1978 | Wallace | 264/528 |
| 4,481,323 A | 11/1984 | Sterling | 524/269 |
| 4,499,045 A | 2/1985 | Obsomer | 264/532 |
| 4,820,349 A | 4/1989 | Saab | 128/344 |
| RE33,561 E | 3/1991 | Levy | 428/36.92 |
| 5,195,970 A | 3/1993 | Gahara | 604/96 |
| 5,223,205 A | 6/1993 | Jackowski et al. | 264/521 |
| 5,254,091 A | 10/1993 | Aliahmad et al. | 604/96 |
| 5,304,340 A | 4/1994 | Downey | 264/521 |
| 5,334,201 A | 8/1994 | Cowan | 623/1 |
| 5,338,298 A | 8/1994 | McIntyre | 604/96 |
| 5,358,486 A * | 10/1994 | Saab | 604/96 |
| 5,409,495 A | 4/1995 | Osborn | 606/108 |
| 5,653,691 A | 8/1997 | Rupp et al. | 604/96 |
| 5,714,110 A * | 2/1998 | Wang et al. | 264/529 |
| 5,755,708 A | 5/1998 | Segal | 604/109 |
| 5,810,871 A | 9/1998 | Tuckey et al. | 606/198 |
| 5,836,965 A | 11/1998 | Jendersee et al. | 606/198 |
| 5,843,116 A | 12/1998 | Crocker et al. | 606/192 |
| 5,871,468 A | 2/1999 | Kramer et al. | 604/96 |
| 5,931,851 A * | 8/1999 | Morales | 29/235 |
| 5,948,345 A * | 9/1999 | Patel et al. | 264/529 |
| 6,024,752 A * | 2/2000 | Horn et al. | 606/192 |
| 6,120,523 A * | 9/2000 | Crocker et al. | 128/898 |
| 6,176,698 B1 * | 1/2001 | Grantz et al. | 249/117 |
| 6,190,590 B1 * | 2/2001 | Randall et al. | 264/138 |
| 6,200,325 B1 * | 3/2001 | Durcan et al. | 604/101.05 |

* cited by examiner

Primary Examiner—Robert Davis
(74) Attorney, Agent, or Firm—Fulwider Patton Lee & Utecht, LLP (57) ABSTRACT

The invention is directed to modular molds for forming an inflatable member, in particular, balloons for use with balloon catheters and stent delivery systems. The detachable molds of the present invention include detachable segments including a generally cylindrical intermediate segment having an intermediate longitudinal dimension and an intermediate interior chamber with an intermediate inner diameter, and proximal and distal segments longitudinally disposed at opposing ends of the intermediate segment and having corresponding interior chambers.

11 Claims, 13 Drawing Sheets

MODULAR MOLD DESIGNS

FIELD OF INVENTION

The invention relates to the field of intravascular delivery systems, and more particularly to modular molds for forming balloon.

BACKGROUND OF THE INVENTION

In percutaneous transluminal coronary angioplasty (PTCA) procedures, a guiding catheter is advanced until the distal tip of the guiding catheter is seated in the ostium of a desired coronary artery. A guide wire, positioned within an inner lumen of an dilatation catheter, is first advanced out of the distal end of the guiding catheter into the patient's coronary artery until the distal end of the guide wire crosses a lesion to be dilated. Then the dilatation catheter having an inflatable balloon on the distal portion thereof is advanced into the patient's coronary anatomy, over the previously introduced guide wire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway.

Generally, the inflated diameter of the balloon is approximately the same diameter as the native diameter of the body lumen being dilated so as to complete the dilatation but not overexpand the artery wall. After the balloon is finally deflated, blood flow resumes through the dilated artery and the dilatation catheter can be removed therefrom.

After angioplasty procedures, restenosis may form in the artery at the original stenotic site, necessitating either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons, the balloon design must be tailored to provide optimal performance for a particular application. An important consideration in the design of the dilatation catheter assemblies is the ability of the balloon to either or both retain and deploy the stent which is mounted thereon.

As such, what has been needed are molds for forming balloons having differing geometries while maintaining efficient manufacturing processes. The present invention satisfies these and other needs.

SUMMARY OF THE INVENTION

The invention is directed to modular molds for forming an inflatable member, in particular, balloons for use with balloon catheters and stent delivery systems. The detachable molds of the present invention include detachable segments including a generally cylindrical intermediate segment having an intermediate longitudinal dimension and an intermediate interior chamber with an intermediate inner diameter, and proximal and distal segments longitudinally disposed at opposing ends of the intermediate segment and having corresponding interior chambers.

In one embodiment the proximal and distal chambers each has a base at a first end adjacent the intermediate chamber and a second end opposite the first end. The proximal and distal chamber bases each includes a ridge sufficiently raised with respect to its adjacent intermediate chamber. The mold has an inner diameter at the proximal and distal ridges sufficiently larger than the inner diameter of the mold at the intermediate segment.

In another embodiment, the proximal and distal chambers each has a base at a first end adjacent the intermediate chamber and a second end opposite the first end. The mold has an inner diameter at the proximal and distal bases sufficiently smaller than the inner diameter of the mold at the intermediate segment. In one embodiment, the mold proximal and distal chambers further include, respectively, proximal and distal steps having vertical segments and disposed between the intermediate chamber and the proximal and distal bases, respectively. Additionally, the mold proximal and distal chambers include proximal and distal shoulder chambers, respectively. The proximal and distal shoulder chambers taper in a direction away from the intermediate chamber and form proximal and distal shoulder chamber angles with the longitudinal axis of the mold, respectively.

In another embodiment, the proximal and distal chambers each has a base at a first end adjacent the intermediate chamber and a second end opposite the first end, and proximal and distal recesses disposed between the intermediate chamber and the proximal and distal bases, respectively. The mold, has an inner diameter at the proximal and distal bases sufficiently smaller than the inner diameter of the mold at the intermediate chamber. The mold has an inner diameter at the proximal and distal recesses sufficiently smaller than the inner diameter of the mold at the proximal and distal bases.

The molds of the present invention can further include detachable proximal and distal extension shafts configured to connect the proximal and distal segments at their respective proximal and distal ends to a blow-molding machine. The molds of the present invention are preferably made from metals, more preferably, stainless steel, for ease of fabrication, to achieve good surface quality and temperature and corrosion resiliency.

Angioplasty and stent delivery balloons are made of polymeric materials. In general, the polymeric material is extruded into tubular shapes or parisons. The extruded tube is then formed into the balloon shape using a blow molding process. Apparatus of the balloon blow molding process comprises a mold, a temperature source, a pressure source, and a tension source. In the balloon molding process, the extruded tubing is placed inside the mold and subsequently, the mold is heated with the temperature source. The tubing is stretched longitudinally using the tension source. The tubing is also expanded radially with the pressure source. The mold is made into multiple parts or inserts with opening lines or parting lines for ease of access. The final balloon shape is mostly controlled by the mold geometric design and the process parameters. The molds are generally made from materials that can be formed into desirable shapes and are geometrically stable at elevated temperatures. The segments may be fabricated using machining methods consistent with the choice of material and quality requirements.

DETAILED DESCRIPTION OF THE INVENTION

Figure 1A:
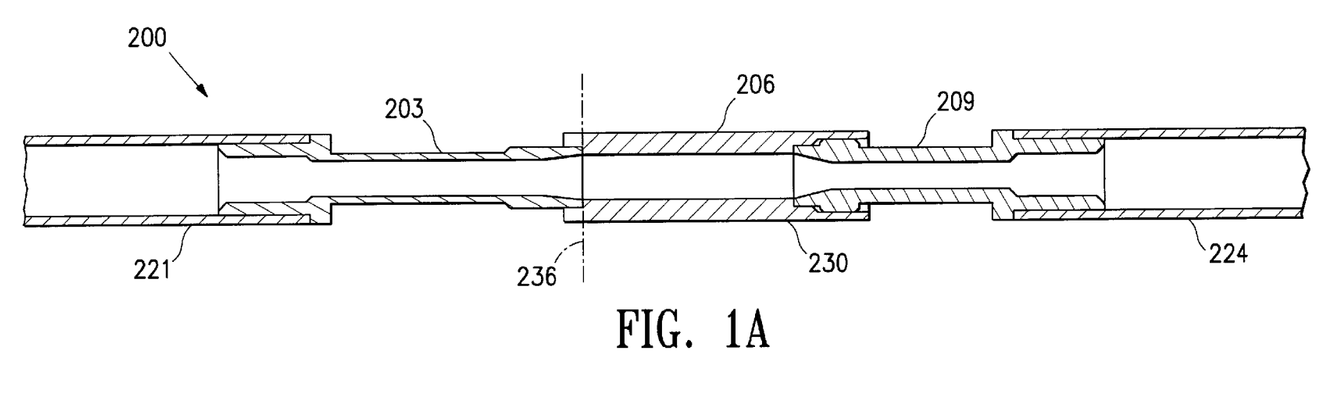
FIG. 1A is a partial longitudinal cross sectional view of a modular mold having multiple segments.
Figure 1B:
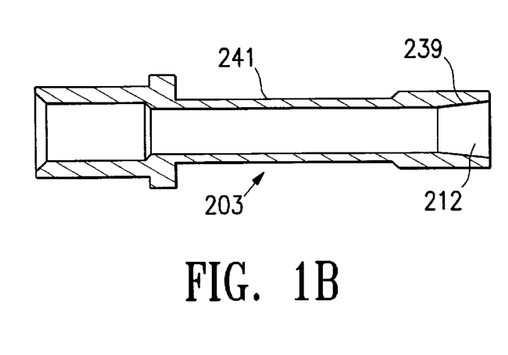
FIG. 1B is a longitudinal cross sectional view of the modular mold of FIG. 1A showing a proximal insert.

FIGS. 1A, B, C, and D illustrate a detachable mold 200 embodying features of the invention, and generally including detachable segments including proximal, intermediate, and distal section inserts, 203, 206, and 209, having proximal, intermediate, and distal interior chambers 212, 215, and 218; respectively. In addition to the proximal, intermediate, and distal section inserts, 203, 206, and 209, there are proximal and distal extension shafts, 221 and 224, used to attach the mold 200 to the blow-molding machine (not shown). The inserts, 203, 206, and 209, are attached together, preferably with threaded fasteners 227, although the means of attachment may be different. Each mold segment includes two halves, such as 230 and 233 for the intermediate mold insert 206. The mold halves for each segment are separated at a parting line 236 by the blow-molding machine. The inserts, 203, 206, and 209, are made from any suitable grade of stainless steel or other suitable materials. The segmented inserts allow easier access for rapid machining to create geometric configurations to form the desired balloon shapes.

The proximal insert 203 of the mold 200 is used primarily for forming a proximal section 83 of a balloon 28; including a proximal shoulder forming portion 239 for forming a proximal shoulder section 94 of the balloon 28, and a proximal shaft forming portion 241 for forming a proximal shaft 106 of the balloon 28, the balloon features, as shown in FIGS. 2 through 8, and described below.

Figure 1C:
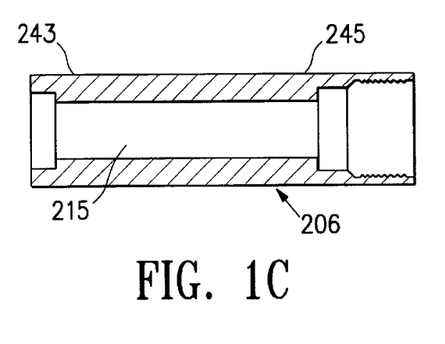
FIG. 1C is a longitudinal cross sectional view of the modular mold of FIG. 1A showing an intermediate insert.

The intermediate insert 206 is primarily used for forming an intermediate section 85 of the balloon 28, and includes an intermediate proximal portion 243 and an intermediate distal portion 245 for forming a proximal intermediate portion 247 and a distal portion 249 of the intermediate section 85 of balloon 28 (FIG. 5), respectively.

Figure 1D:
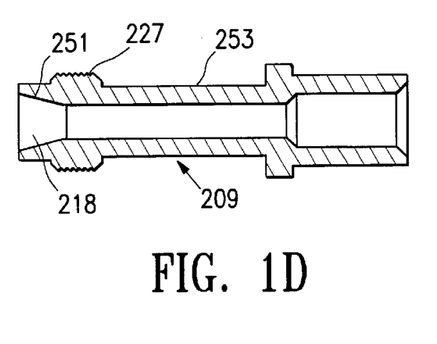
FIG. 1D is a longitudinal cross sectional view of the modular mold of FIG. 1A showing a distal insert.

The distal insert 209 of the mold 200 is used for forming a distal section 84 of the balloon 28; including a distal shoulder forming portion 251 for forming a distal shoulder section 100 of the balloon 28, and a distal shaft forming portion 253 for forming a distal shaft 109 of the balloon 28.

Alternatively, the proximal and distal inserts 203 and 206 may further include the intermediate proximal portion 243 and the distal intermediate portion 245, respectively. Similarly, the intermediate insert 206 may further include proximal and distal shoulders formation portions 239 and 251 (FIGS. 1B, 1D) for forming proximal and distal shoulders sections 94 and 100 of balloon 28.

Figure 8A:
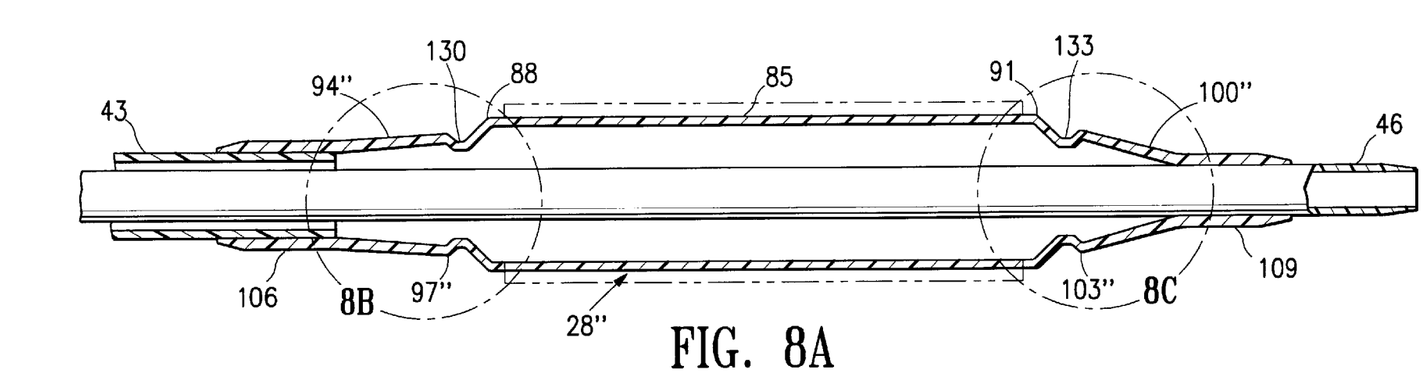
FIG. 8A is a partial longitudinal cross sectional view of an alternative embodiment of a delivery system showing an unwrapped balloon having proximal and distal recesses formed between intermediate section and proximal and distal shoulders.
Figure 8B:
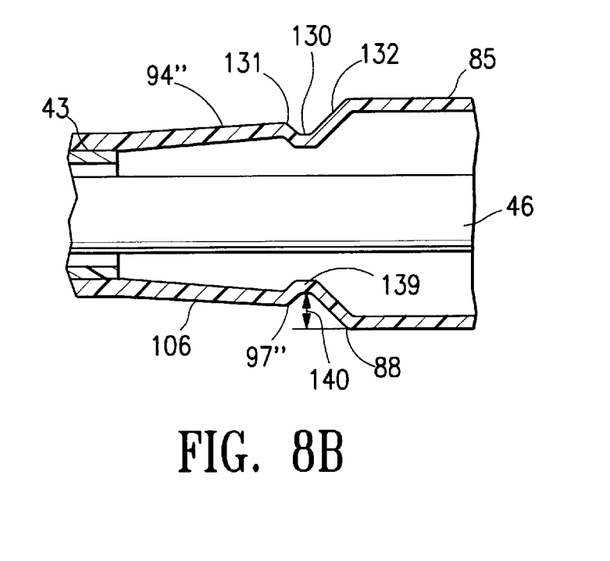
FIG. 8B is an enlarged view of the delivery system of FIG. 8A showing the proximal recess of the balloon.
Figure 8C:
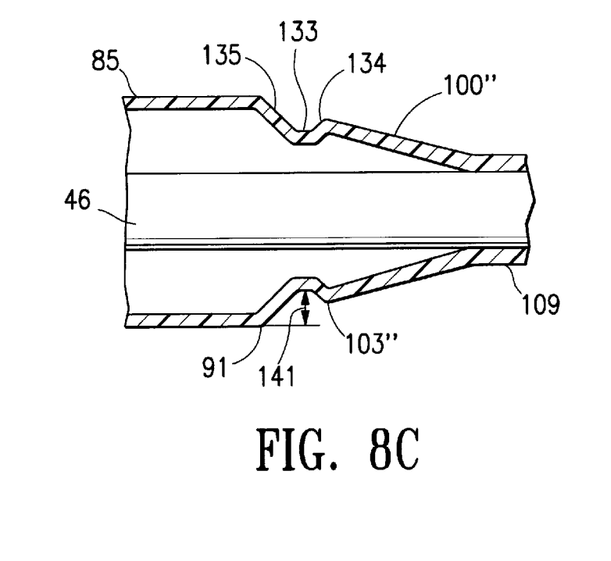
FIG. 8C is an enlarged view of the delivery system of FIG. 8A showing the distal recess of the balloon.
Figure 9A:
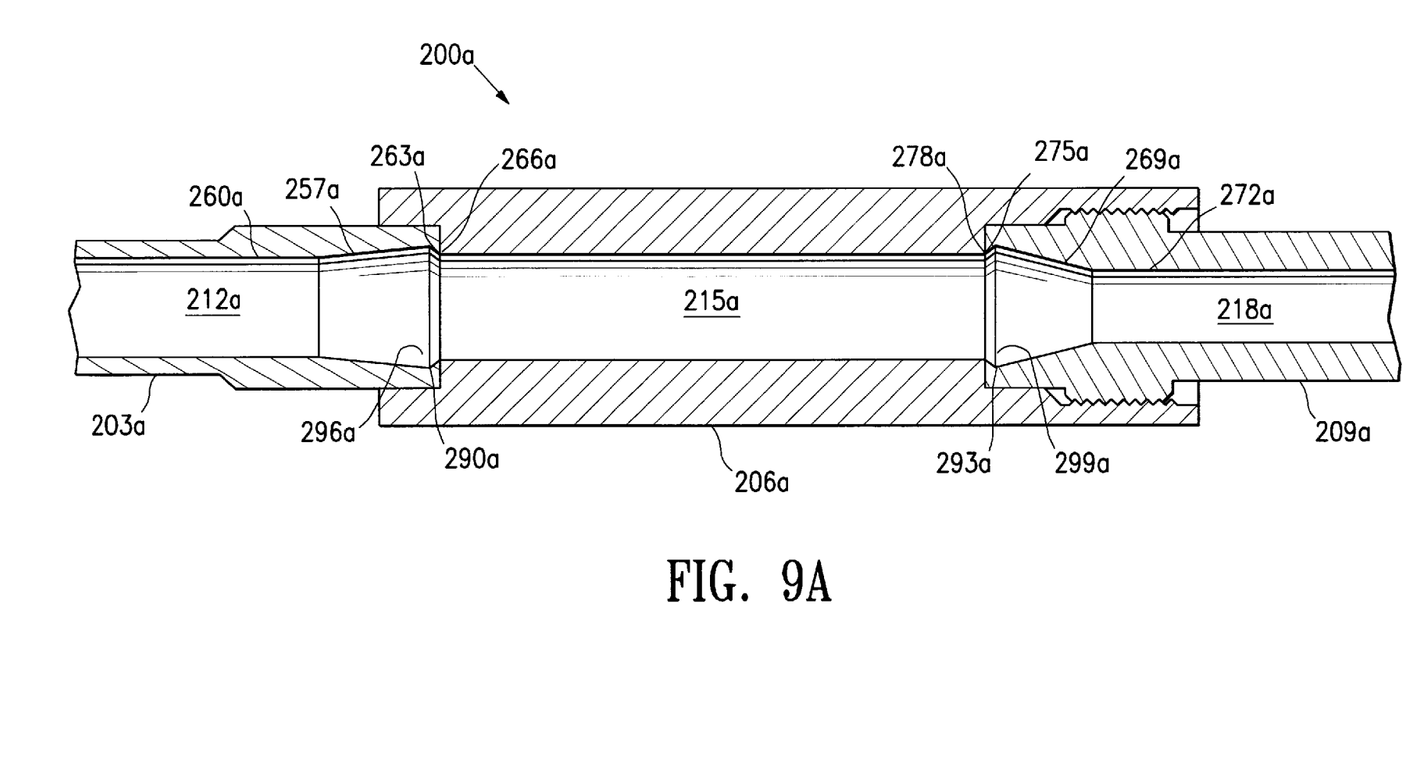
FIG. 9A is a partial longitudinal cross sectional view of a modular mold having multiple segments and having proximal and distal ridges.
Figure 9B:
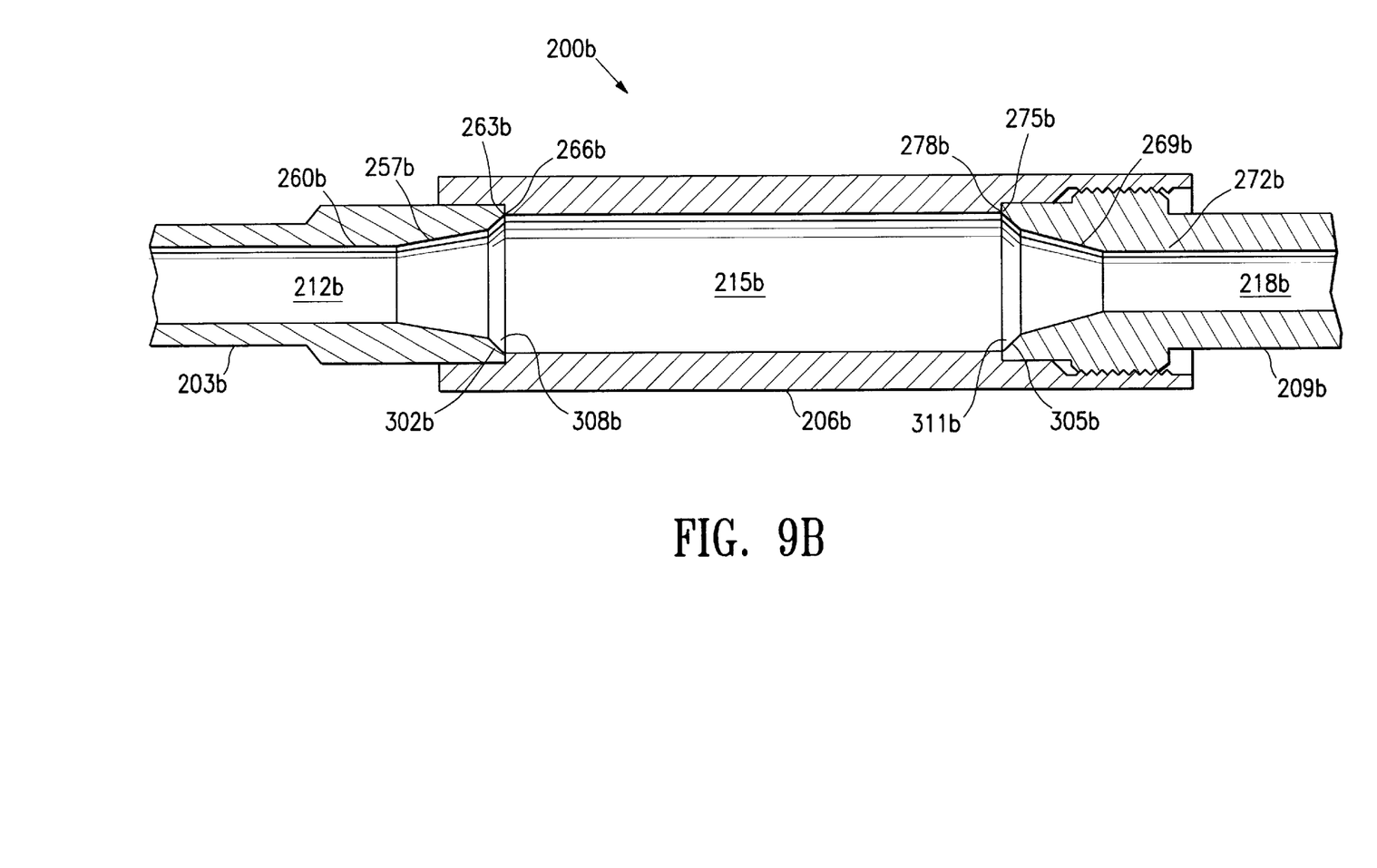
FIG. 9B is a partial longitudinal cross sectional view of a modular mold having multiple segments and having proximal and distal steps.
Figure 9C:
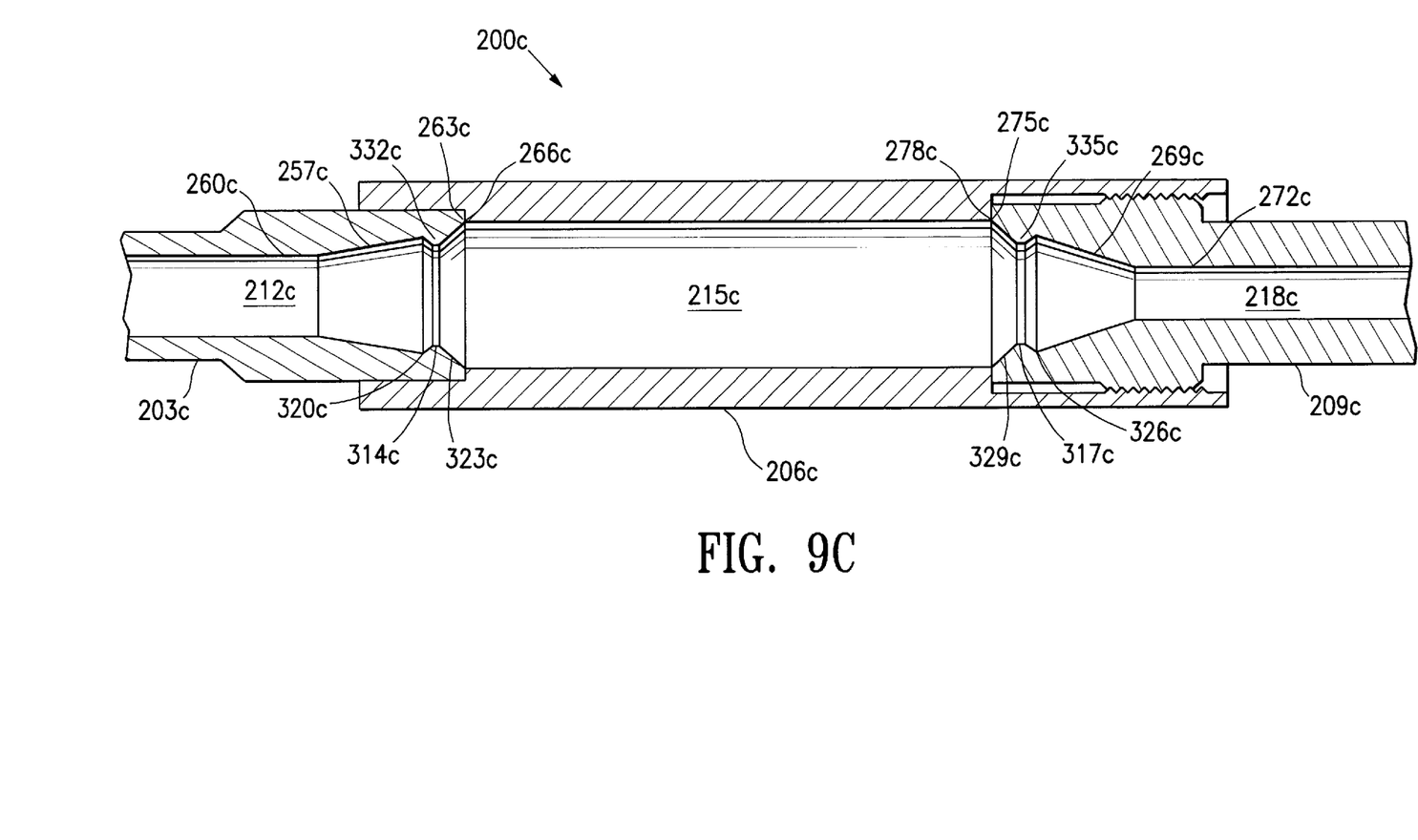
FIG. 9C is a partial longitudinal cross sectional view of a modular mold having multiple segments and having proximal and distal recesses.
Figure 10A:
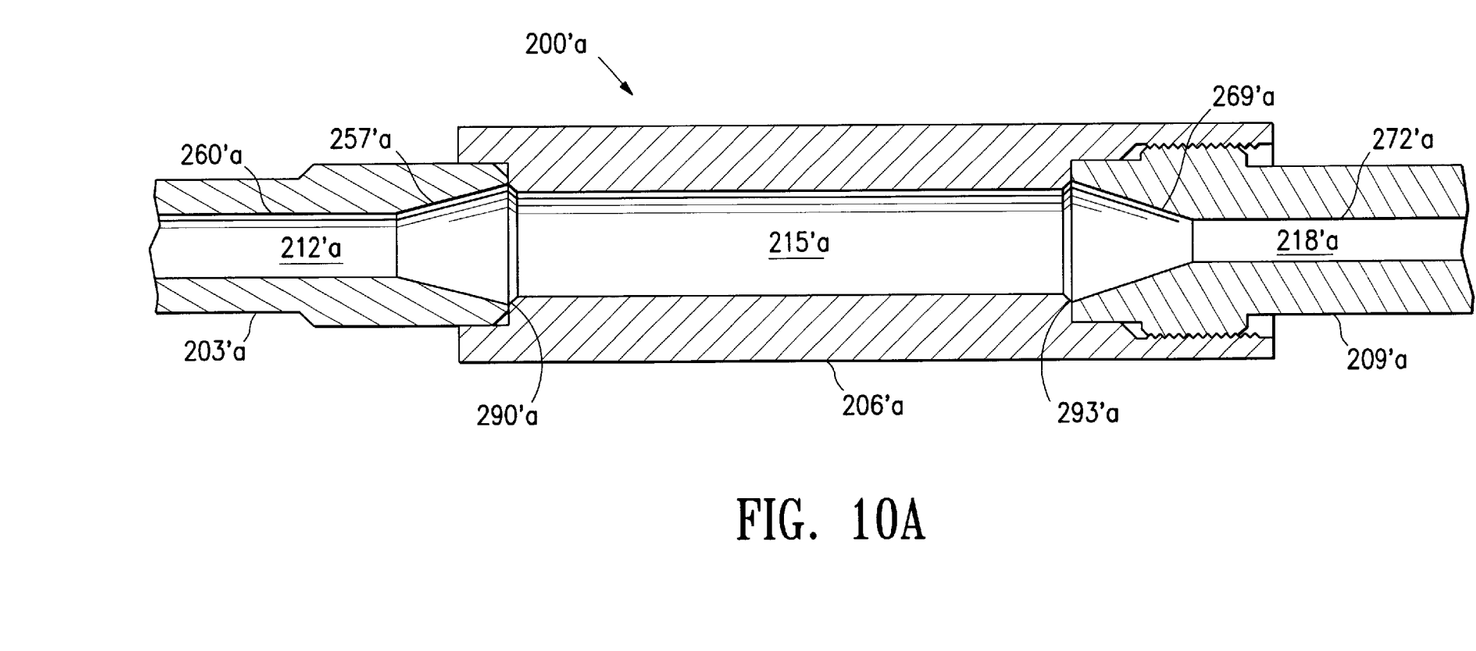
FIG. 10A is a partial longitudinal cross sectional view of another embodiment of modular mold of FIG. 9A.
Figure 10B:
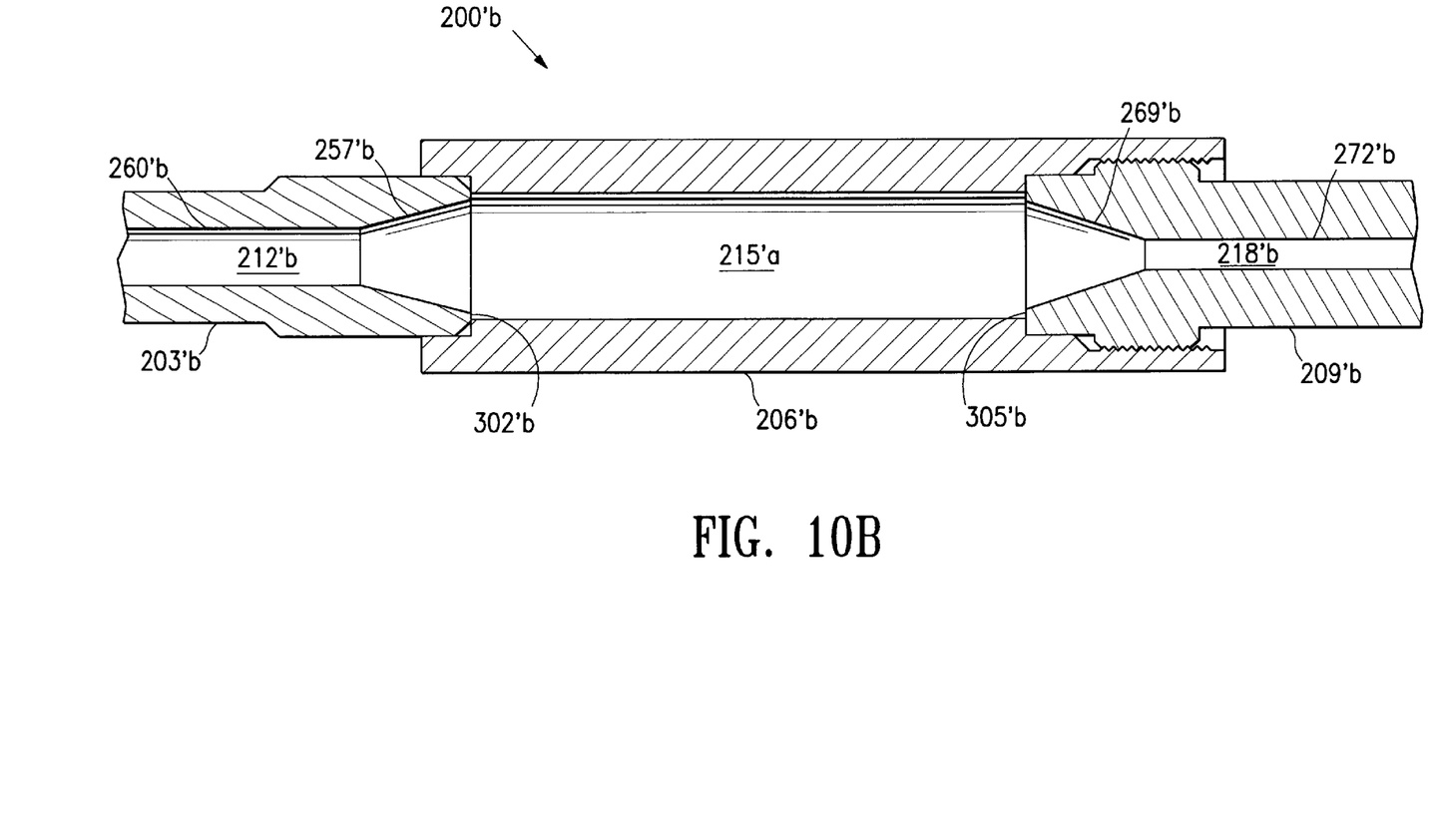
FIG. 10B is a partial longitudinal cross sectional view of another embodiment of modular mold of FIG. 9B.
Figure 10C:
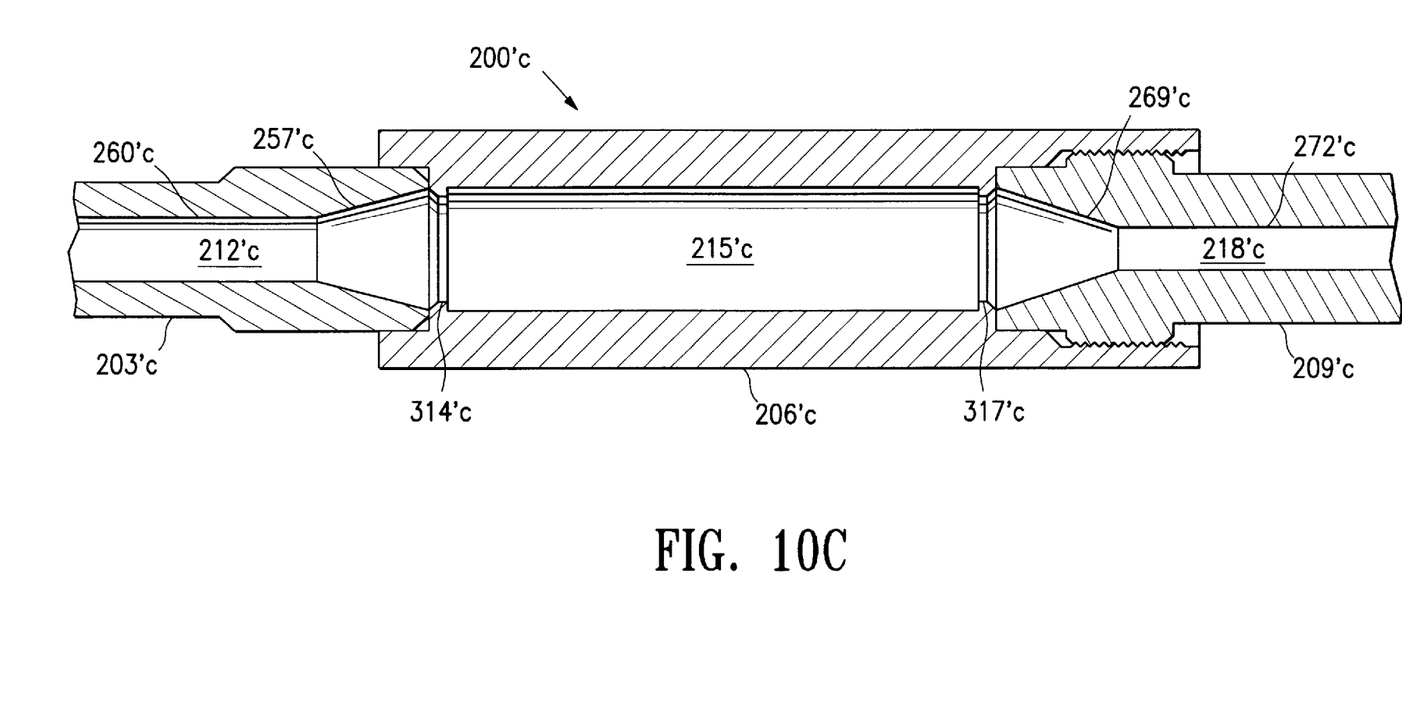
FIG. 10C is a partial longitudinal cross sectional view of another embodiment of modular mold of FIG. 9C.

The mold 200 can be used to form balloons having any desirable configuration. In alternate embodiments, the mold 200 can be designed, as shown in FIGS. 9–10, to form balloons having specific configurations, features of which are illustrated in FIGS. 2–8. The balloon designs will be discussed first.

Figure 2:
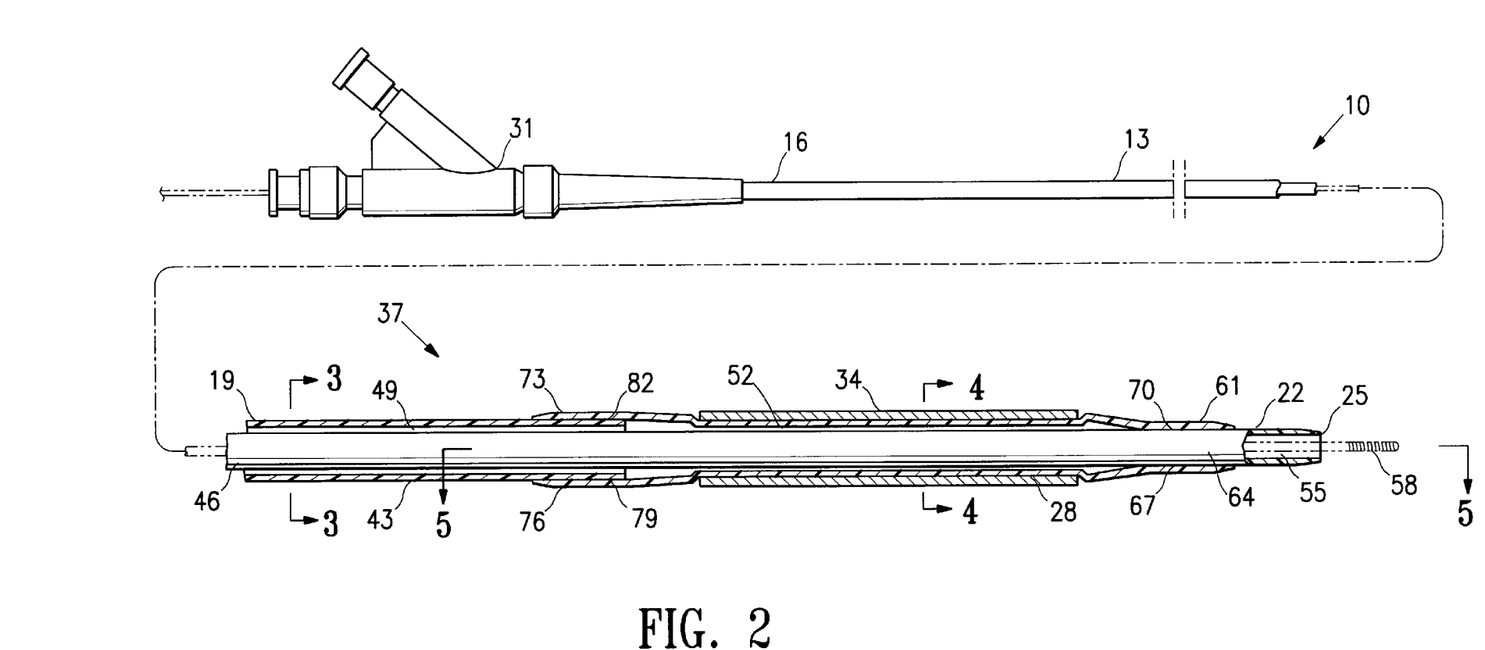
FIG. 2 is a longitudinal cross sectional view of a stent delivery system showing a wrapped balloon with ridges formed between intermediate section and proximal and distal shoulders.

FIG. 2 illustrates a balloon catheter 10 generally including, an elongated catheter shaft 13 having a proximal section 16 and a distal section 19 with a distal end 22 and a distal tip 25, the inflatable balloon 28 on the distal section 19 of the catheter shaft 13, and an adapter 31 mounted on the proximal section 16 of the catheter shaft 13. In the embodiment illustrated in FIG. 2, the balloon catheter 10 has a stent 34 mounted on the balloon 28 to form a stent delivery catheter system 37. In FIG. 2, the catheter system 37 is illustrated prior to expansion of the wrapped balloon 28, with the balloon 28 and stent 34 in a low profile, unexpanded state for advancement within the patient.

Figure 3:
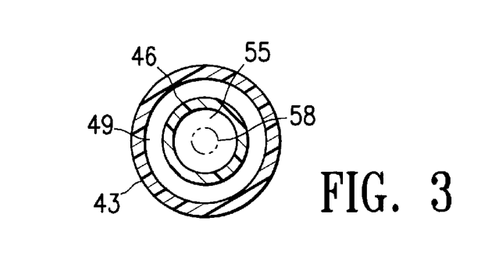
FIG. 3 is a transverse cross sectional view of the delivery system of FIG. 2 taken along line 3—3.
Figure 4:
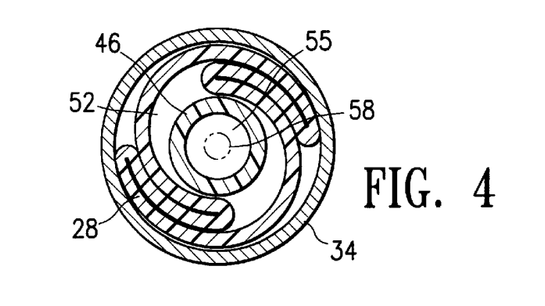
FIG. 4 is a transverse cross sectional view of the delivery system of FIG. 2 taken along line 4—4.

In the embodiment illustrated in FIG. 2, the catheter shaft 13 has an outer tubular member 43 and an inner tubular member 46 disposed within the outer tubular member 43 and defining, with the outer tubular member, an inflation lumen 49. The inflation lumen 49 is in fluid communication with an interior chamber 52 of the balloon 28. The inner tubular member 46 has an inner lumen 55 extending therein configured to slidably receive a guidewire 58 (shown in phantom) suitable for advancement through a patient's vasculature. A distal extremity 61 of the balloon 28 is sealingly secured to a distal extremity 64 of the inner tubular member 46 to form a distal seal 67 at distal junction 70 and a proximal extremity 73 of the balloon 28 is sealingly secured to a distal extremity 76 of the outer tubular member 43 to form a proximal seal 79 at a proximal junction 82. FIGS. 3 and 4 illustrate transverse cross sectional view of the catheter system 37 shown in FIG. 2, taken along lines 3—3 and 4—4, respectively.

Figure 5:
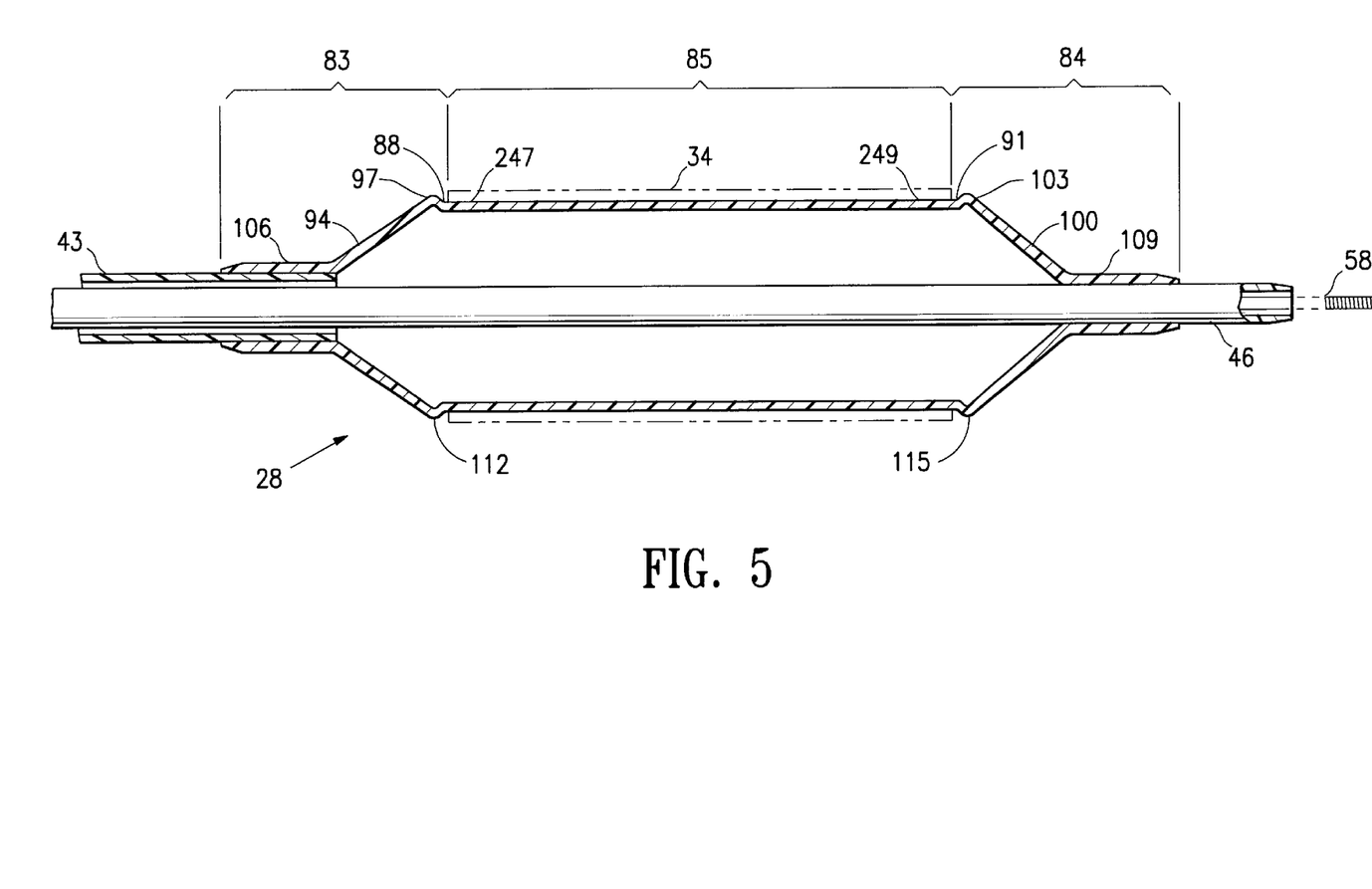
FIG. 5 is a partial longitudinal cross sectional view of the delivery system of FIG. 2 showing the unwrapped balloon in the inflated condition.

As best illustrated in FIG. 5, with the balloon 28 inflated with the wings unwrapped, the balloon 28 includes the proximal and distal sections, 83 and 84, and the intermediate section 85 located therebetween, preferably centrally, with proximal and distal intermediate ends, 88 and 91, for receiving the stent 34 on all or a portion of the intermediate section 85. The proximal section 83 of the balloon 28 includes the proximal shoulder segment 94 with a base 97 adjacent the proximal end 88 of the intermediate section 85. The distal section 84 of the balloon 28 includes the distal shoulder segment 100 with a base 103 adjacent the distal end 91 of the intermediate section 85. The proximal and distal shoulder sections, 94 and 100, taper down from their respective bases 97 and 103, to the proximal and distal shafts 106 and 109, of the proximal and distal sections 83 and 84, respectively. The proximal and the distal balloon shafts, 106 and 109, are secured to the outer tubular member 43 and the inner tubular member 46, respectively, using a variety of suitable means such as adhesive and fusion bonding.

Figure 6A:
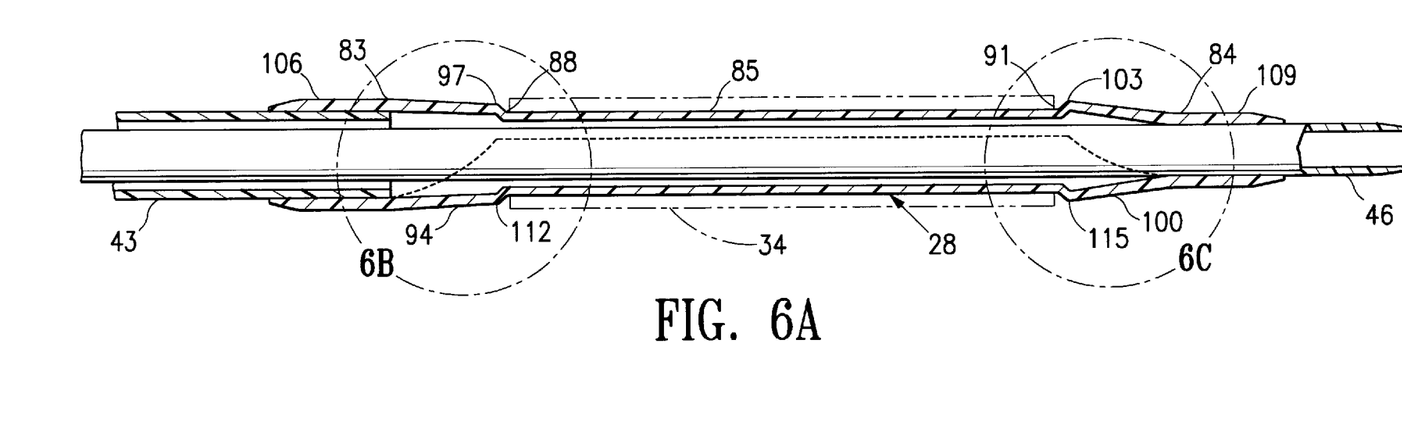
FIG. 6A is a partial longitudinal cross sectional view of the delivery system of FIG. 2 showing the wrapped balloon.
Figure 6B:
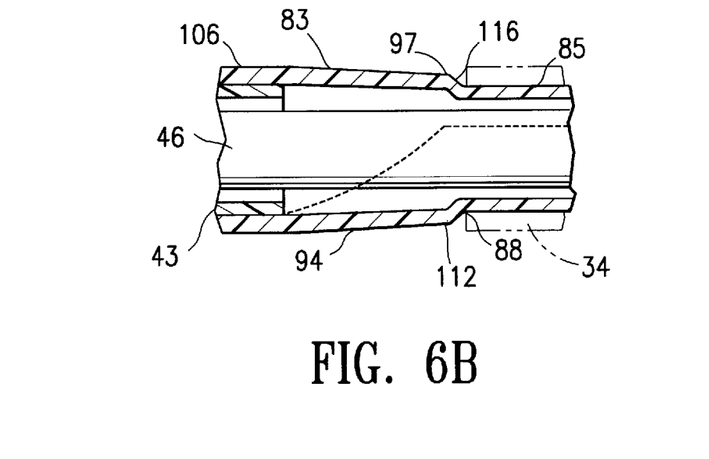
FIG. 6B is an enlarged view of the delivery system of FIG. 6A showing the proximal ridge of the balloon.
Figure 6C:
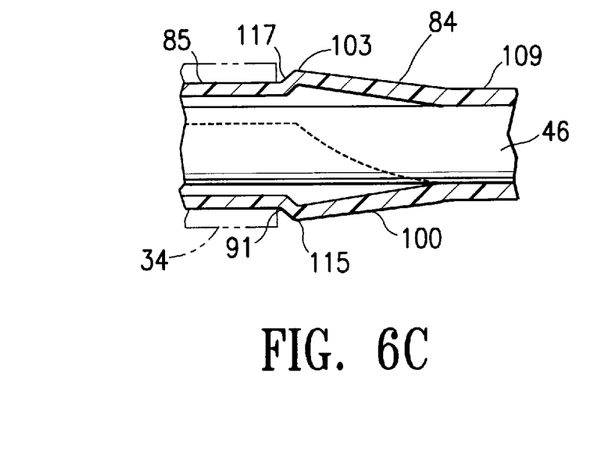
FIG. 6C is an enlarged view of the delivery system of FIG. 6A showing the distal ridge of the balloon.

In the embodiment, best illustrated in FIGS. 6A, 6B, and 6C, the proximal and distal shoulder segments 94 and 100 of the balloon 28, at their respective bases, 97 and 103, have a sufficiently larger diameter than the outer diameter of the balloon 28 at proximal and distal intermediate ends 88 and 91, respectively, and include proximal and distal ridges, 112 and 115. The proximal and distal ridges, 112 and 115, are sufficiently raised with respect to the intermediate section 85 at its proximal and distal ends 88 and 91 so as to enhance the retention of the stent 34, when present, on the balloon 28. The proximal and distal ridges, 112 and 115, capture the crimped stent therebetween, and minimize the longitudinal movement of the stent 34, thus minimizing the unwanted sliding of the stent 34 off the balloon 28. The proximal and distal ridges 112 and 115 have a height 116 and 117 with respect to the proximal and distal intermediate ends 88 and. 91, respectively, such that, preferably, the outside diameter of the balloon as measured radially along the proximal and distal ridges 112 and 115 is greater than the outside diameter of the balloon measured at the intermediate section 85. Preferably, the ridge height 116 and 117 (i.e., the dimension above the intermediate section 85). is less than the thickness of the stent 34. As such, when the balloon is inflated within the interior wall of the artery, the ridges 112 and 115 do not come in contact with the wall. In a preferred embodiment, the ridge height 115 and 117 ranges from about zero to about 0.1 millimeters (mm), preferably, from about 0.05 to about 0.1 mm. In one embodiment, the longitudinal dimension of stent 34 (i.e., the distance between the intermediate section proximal and distal ends 88 and 91) is equal to or less than the longitudinal dimension of the intermediate section 85, as for example, less by about 0.1 mm.

Figure 7A:
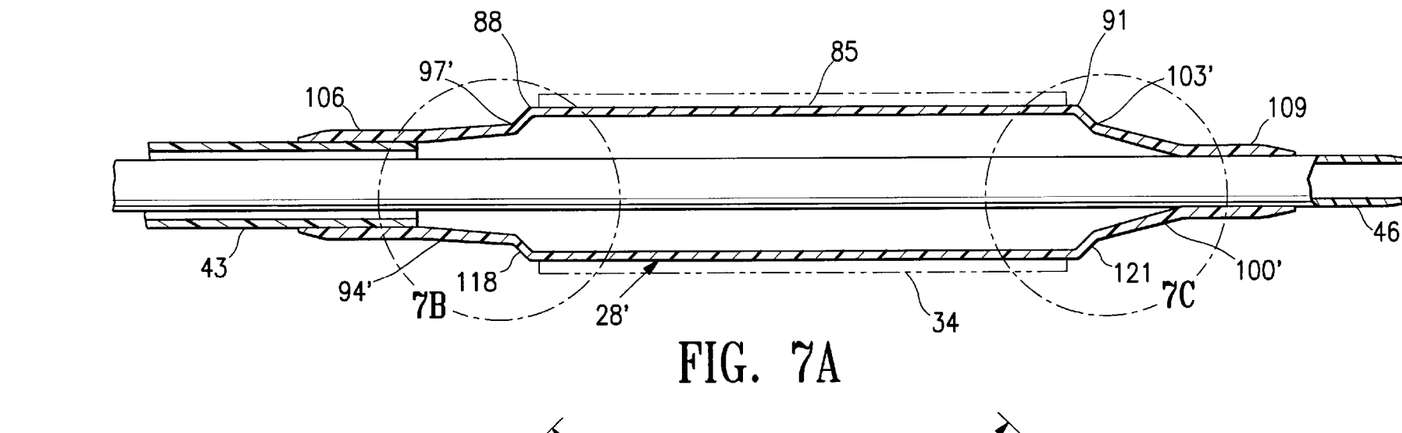
FIG. 7A is a partial longitudinal cross sectional view of an alternative embodiment of a delivery system showing an unwrapped balloon having proximal and distal steps formed between intermediate section and proximal and distal shoulders.
Figure 7B:
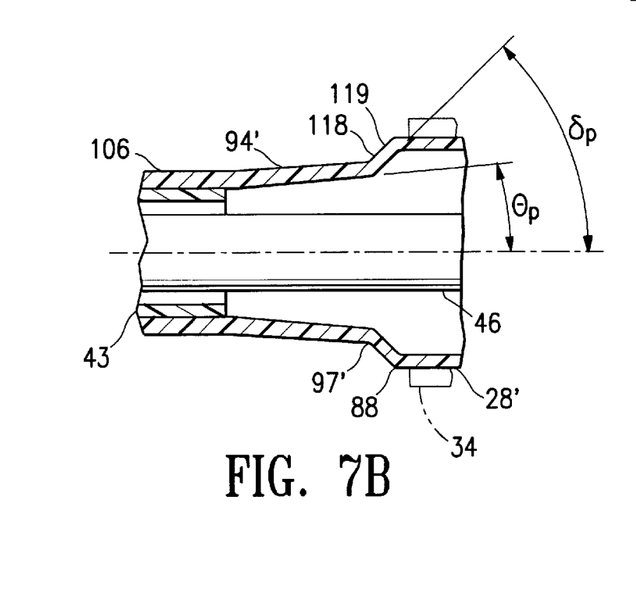
FIG. 7B is an enlarged view of the delivery system of FIG. 7A showing the proximal step of the balloon.
Figure 7C:
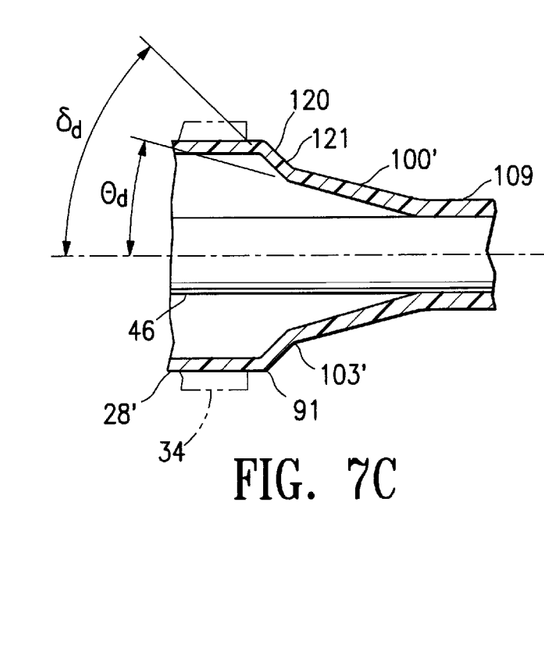
FIG. 7C is an enlarged view of the delivery system of FIG. 7A showing the distal step of the balloon.

In the embodiment, best illustrated in FIGS. 7A, 7B, and 7C, proximal and distal shoulder segments 94' and 100' of a balloon 28', at their respective bases, 97' and 103', have a sufficiently smaller outer diameter than the outer diameter of the balloon 28' at proximal and distal intermediate ends 88 and 91, respectively, and include proximal and distal steps, 118 and 121 having vertical segments, 119 and 120. The vertical segments 119 and 120, preferably, have a height such that the outside diameter of the balloon 28' as measured radially along the proximal and distal bases 97' and 103' is less than the outside diameter of the balloon 28' measured at the intermediate section 85. As such, when the balloon is inflated within the interior wall of the artery, the proximal and distal shoulder segments 94' and 100' do not come in contact with the interior wall of the artery. The vertical segments 119 and 120 may have a height ranging from about zero to about 1.4 mm. Some exemplary dimensions of the outside diameter of the balloon, in an inflated state, measured at the intermediate section 85 and the vertical segments 119 and 120 heights are:

| Balloon OD measured along intermediate segment 85 (mm) | Vertical segments 119 and 120 heights (mm) as measured in a 90° angle from the base 97' and 103' |
| --- | --- |
| 2.0 | 0–0.6 |
| 2.5 | 0–0.8 |
| 3.0 | 0–1.0 |
| 3.5 | 0–1.2 |
| 4.0 | 0–1.4 |

The proximal and distal shoulder segments 94' and 100' may form a shoulder angle θ with the longitudinal axis of the balloon ranging from 10° to 45° with proximal and distal shoulder angles $\theta_p$ and $\theta_d$ being equal or differing from one another. The steps 18 and 121 form a step angle δ, preferably about 90°, with the proximal and distal bases 97' and 103' of the proximal and distal shoulder segments 94' and 100' (or with the longitudinal axis of the balloon). The step angles δ can be less than 90°, but no less than the shoulder angles θ. Proximal and distal step angles $\delta_p$ and $\delta_d$ may be equal or may differ from one another.

The balloon 28' at its proximal and distal shoulder bases, 97' and 103', is sufficiently lower with respect to the intermediate section 85 at its proximal and distal ends 88 and 91 so as to enhance the ease of deployment of the stent 34 from the balloon 28'. Upon the expansion of the balloon 28', the proximal and distal shoulders 94' and 100' are expanded to an outer diameter smaller than the outer diameter of the intermediate section 85 at its proximal and distal ends, 88 and 91, respectively, thereby, enhancing the deployment of the stent 34. Additionally, the vertical segments 119 and 120 provide visual aide for the alignment of the Stent 34 during stent installation onto the balloon 28', as well as minimizing contact between the interior wall of the artery and the proximal and distal shoulders 94' and 100'.

In the embodiment, best illustrated in FIGS. 8A, 8B, 8C, 8D, and 8E, a balloon 28" includes proximal and distal recesses 130 and 133, disposed between a proximal shoulder base 97" and proximal intermediate end 88; and between the distal intermediate end 91 and a distal shoulder base 103";

respectively. The proximal recess 130 includes a proximal ridge 131 and a proximal step 132 adjacent the proximal intermediate end 88 and being at an end opposite the proximal ridge 131. Similarly, the distal recess 133 includes a distal ridge 134 and a distal step 135 adjacent the distal intermediate end 91 and being at an end opposite the distal ridge 134. The proximal and distal ridges, 131 and 134, minimize the sliding of the stent 34, when present, while it is crimped on the wrapped balloon 28", while proximal and distal steps, 132 and 135, enhance the ease of deployment of stent 34.

The balloon 28" at the proximal and distal recesses, 130 and 133, preferably, has a longitudinal dimension equal to or greater than a wall thickness 139 of the balloon 28" measured at the proximal and distal recesses, 130 and 133. The balloon 28 at the proximal and distal recesses, 130 and 133, has an outer diameter smaller than the outer diameter of the balloon 28" at the corresponding proximal and distal intermediate ends, 88 and 91. Preferably, the proximal and distal recesses 130 and 133 have a depth 140 and 141 with respect to the proximal and distal intermediate ends 88 and 91, respectively, ranging from about 0.05 to about 0.15 mm, more preferably, from about 0.1 to about 0.15 mm.

Figure 8D:
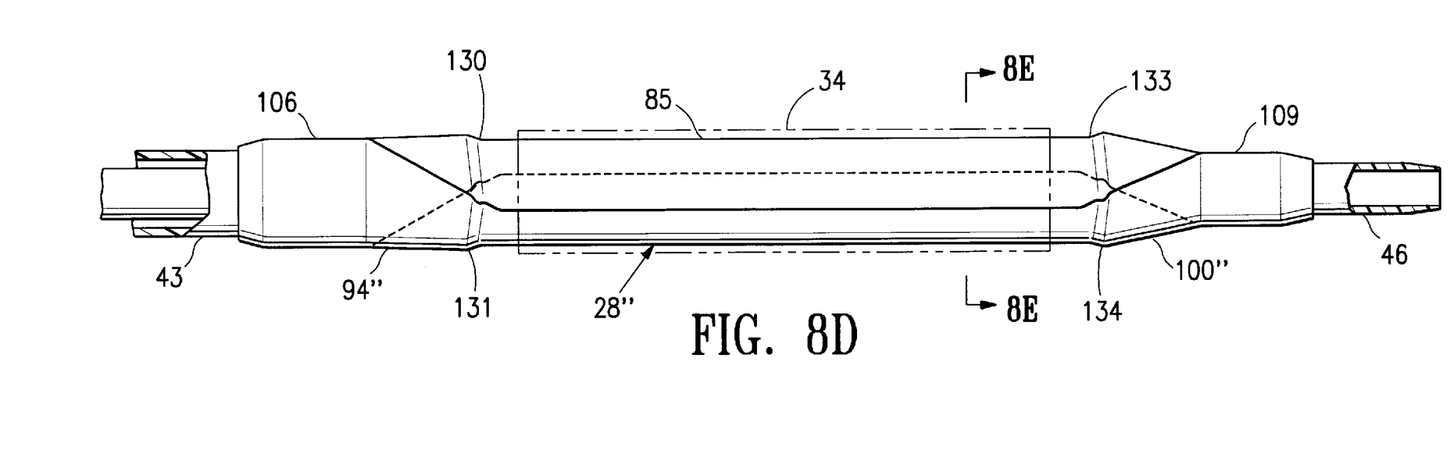
FIG. 8D is a partial longitudinal cross sectional view of the delivery system of FIG. 8A showing the balloon in a wrapped condition.
Figure 8E:
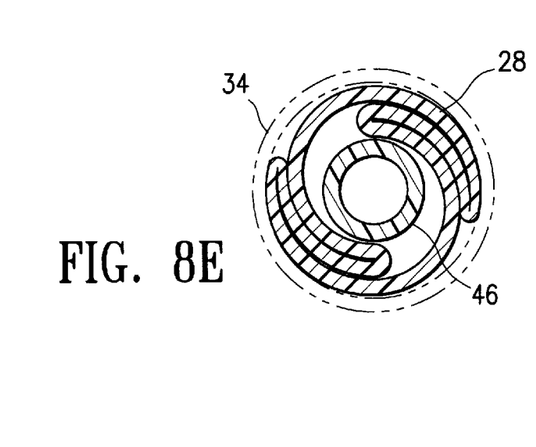
FIG. 8E is a transverse cross sectional view of the delivery system of FIG. 8D taken along line 8E—8E.

The balloon 28", when wrapped as shown in FIGS. 8D and 8E, at the proximal and distal ridges, 131 and 134, has a diameter sufficiently larger than the outer diameter of the balloon 28" at proximal and distal intermediate sections 88 and 91. The proximal and distal ridges, 131 and 134, when wrapped, are sufficiently raised with respect to the intermediate section 85 at its proximal and distal ends 88 and 91 so as to enhance the retention of the stent 34 on the balloon 28". When the balloon is unwrapped (as for example when it is inflated), as shown in FIG. 8A, the outer diameter of the balloon 28" at the proximal and distal shoulders 94" and 100" and their respective proximal and distal ridges 131 and 134, is sufficiently smaller than the outer diameter of the balloon 28" at proximal and distal intermediate ends, 88 and 91 to facilitate the deployment of the balloon upon inflation.

Now referring to FIGS. 9A, B, and C, molds 200(*a*), 200(*b*), and 200(*c*), shown in an attached configuration, illustrate features of the modular molds of the present invention with interior chambers specifically designed to manufacture the balloons illustrated in FIGS. 6A, 7A, and 8A, respectively.

As illustrated in FIGS. 9A, B, and C, in addition to extension shafts (not shown—see FIG. 1A) each mold 200(*a*), 200(*b*), and 200(*c*) includes proximal, intermediate, and distal inserts, 203(*a*), 206(*a*), 209(*a*); 203(*b*), 206(*b*), 209(*b*); and 203(*c*), 206(*c*), 209(*c*); respectively.

As shown in FIG. 9A the proximal insert 203(*a*) of mold 200(*a*) includes proximal shoulder and shaft sections, 257(*a*) and 260(*a*). The proximal shoulder 257(*a*) has a proximal base 263(*a*) which when the proximal insert 203(*a*) is attached to the intermediate section insert 206(*a*) as shown in FIG. 9A, will be adjacent a proximal intermediate end 266(*a*) of the intermediate section 206(*a*). Similarly, the distal insert 209(*a*) of mold 200(*a*) includes distal shoulder and shaft sections, 269(*a*) and 272(*a*). The distal shoulder 269(*a*) has a distal base 275(*a*) which when the distal insert 209(*a*) is attached to the intermediate section insert 206(*a*) as shown in FIG. 9B, will be adjacent a distal intermediate end 278(*a*) of the intermediate section 206(*a*).

Interior chambers, 212(*a*) and 218(*a*), of the proximal and distal shoulder inserts, 203(*a*) and 209(*a*), at their respective proximal and distal bases, 263(*a*) and 275(*a*), have a sufficiently larger inner diameter than the inner diameter of an interior chamber 215(*a*) of the intermediate insert 206(*a*) at its proximal and distal intermediate ends, 266(*a*) and 278(*a*), respectively, and include proximal and distal ridges, 290(*a*) and 293(*a*). The proximal and distal ridges, 290(*a*) and 293(*a*), are sufficiently raised with respect to the intermediate insert proximal and distal ends, 266(*a*) and 278(*a*). The proximal and distal ridges, 290(*a*) and 293(*a*), have a height 296(*a*) and 299(*a*) with respect to the intermediate insert proximal and distal ends 266(*a*) and 278(*a*), respectively, ranging from about zero to about 0.1 mm, preferably, from about 0.05 mm to about 0.1 mm.

As shown in FIG. 9B the proximal insert 203(*b*) of mold 200(*b*) includes proximal shoulder and shaft sections, 257(*b*) and 260(*b*). The proximal shoulder 257(*b*) has a proximal base 263(*b*) which when the proximal insert 203(*b*) is attached to the intermediate section insert 206(*b*) as shown in FIG. 9B, will be adjacent a proximal intermediate end 266(*b*) of the intermediate section 206(*b*).

Similarly, the distal insert 209(*b*) of mold 200(*b*) includes distal shoulder and shaft sections, 269(*b*) and 272(*b*). The distal shoulder 269(*b*) has a distal base 275(*b*) which when the distal insert 209(*b*) is attached to the intermediate section insert 206(*b*) as shown in FIG. 9B, will be adjacent a distal intermediate end 278(*b*) of the intermediate section 206(*b*).

Interior chambers, 212(*b*) and 218(*b*), of the proximal and distal shoulder inserts 203(*b*) and 209(*b*), at their respective proximal and distal bases, 263(*b*) and 275(*b*), have a sufficiently smaller inner diameter than the inner diameter of an interior chamber 215(*b*) of the intermediate insert 206(*b*) at its proximal and distal intermediate ends, 266(*b*) and 278(*b*), respectively, and include proximal and distal steps, 302(*b*) and 305(*b*). The proximal and distal steps, 302(*b*) and 305(*b*), have a height 308(*b*) and 311(*b*) with respect to the intermediate insert proximal and distal ends 266(*b*) and 278(*b*), respectively, sufficient for blow molding a balloon of interest.

As shown in FIG. 9C the proximal insert 203(*c*) of mold 200(*c*) includes proximal shoulder and shaft sections, 257(*c*) and 260(*c*). The proximal shoulder 257(*c*) has a proximal base 263(*c*) which when the proximal insert 203(*c*) is attached to the intermediate section insert 206(*c*) as shown in FIG. 9C, will be adjacent a proximal intermediate end 266(*c*) of the intermediate section 206(*c*).

Similarly, the distal insert 209(*c*) of mold 200(*c*) includes distal shoulder and shaft sections, 269(*c*) and 272(*c*). The distal shoulder 269(*c*) has a distal base 275(*c*) which when the distal insert 209(*c*) is attached to the intermediate section insert 206(*c*) as shown in FIG. 9C, will be adjacent a distal intermediate end 278(*c*) of the intermediate section 206(*c*).

Interior chambers, 212(*c*) and 218(*c*), of the proximal and distal shoulder inserts 203(*c*) and 209(*c*), at their respective proximal and distal bases, 263(*c*) and 275(*c*), include proximal and distal recesses, 314(*c*) and 317(*c*), disposed between the proximal shoulder base 263(*c*) and intermediate insert proximal end 266(*c*); and between the distal shoulder base 275(*c*) and intermediate insert distal end 278(*c*); respectively. The proximal recess 314(*c*) includes proximal ridge 320(*c*) and proximal step 323(*c*) adjacent the intermediate insert proximal end 266(*c*) and being at an end opposite the proximal ridge 320(*c*). Similarly, the distal recess 317(*c*) includes distal ridge 326(*c*) and distal step 329(*c*) adjacent the intermediate insert distal end 278(*c*) and being at an end opposite the distal ridge 326(*c*).

The proximal and distal recesses, 314(*c*) and 317(*c*), preferably, have a longitudinal dimension ranging from about 0.05 mm to about 0.15, preferably, ranging from about 0.1 to about 0.15 mm. The proximal and distal recesses, 314(c) and 317(c), have an inner diameter smaller than the inner diameter of the intermediate insert 206(c) at its proximal and distal intermediate insert ends, 266(c) and 278(c). The proximal and distal recesses 314(c) and 317(c), have a depth 332(c) and 335(c) with respect to the proximal and distal intermediate insert ends 266(c) and 278(c), respectively, ranging from about zero to about 0.1 millimeters (mm), preferably, from about 0.05 to about 0.1 mm.

Alternatively, the intermediate inserts 206(a), 206(b), and 206(c) of molds 200(a), 200(b), and 200(c), respectively, may be modified as shown in FIGS. 10A, 10B, and 10C: mold 200'(a) includes intermediate insert 206'(a) having proximal and distal ridges 290'(a) and 293'(a); mold 200'(b) includes intermediate insert 206'(b) having proximal and distal steps 303'(b) and 305'(b); mold 200'(c) includes intermediate insert 206'(c) having proximal and distal recesses 314'(c) and 317'(c).

While particular forms of the invention have been illustrated and described, it will be apparent that various modifications can be made without departing from the spirit and scope of the invention. Accordingly, it is not intended that the invention be limited, except as by the appended claims.

What is claimed is:

1. A mold for forming an inflatable member, comprising:
a generally cylindrical intermediate segment having an intermediate longitudinal dimension and an intermediate interior chamber with an intermediate inner diameter; and
proximal and distal segments longitudinally disposed at opposing ends of the intermediate segment and having corresponding interior chambers, the proximal, intermediate, and distal segments being detachable, wherein the proximal and distal chambers each has a base at a first end adjacent the intermediate chamber and a second end opposite the first end, the proximal and distal chamber bases each including a ridge sufficiently raised with respect to its adjacent intermediate chamber, the mold having an inner diameter at the proximal and distal ridges sufficiently larger than the inner diameter of the mold at the intermediate segment.

2. A mold for forming an inflatable member, comprising:
a generally cylindrical intermediate segment having an intermediate longitudinal dimension and an intermediate interior chamber with an intermediate inner diameter; and
proximal and distal segments longitudinally disposed at opposing ends of the intermediate segment and having corresponding interior chambers, the proximal, intermediate, and distal segments being detachable, wherein the proximal and distal chambers each has a base at a first end adjacent the intermediate chamber and a second end opposite the first end, the mold having an inner diameter at the proximal and distal bases sufficiently smaller than the inner diameter of the mold at the intermediate segment, and wherein the mold proximal and distal chambers further include, respectively, proximal and distal steps having vertical segments and disposed between the intermediate chamber and the proximal and distal bases, respectively, and wherein the mold proximal and distal chambers include proximal and distal shoulder chambers, respectively, the proximal and distal shoulder chambers tapering in a direction away from the intermediate chamber and forming proximal and distal shoulder chamber angles with the longitudinal axis of the mold, respectively.

3. A mold for forming an inflatable member, comprising:
a generally cylindrical intermediate segment having an intermediate longitudinal dimension and an intermediate interior chamber with an intermediate inner diameter; and
proximal and distal segments longitudinally disposed at opposing ends of the intermediate segment and having corresponding interior chambers, the proximal, intermediate, and distal segments being detachable, wherein the proximal and distal chambers each has a base at a first end adjacent the intermediate chamber and a second end opposite the first end, proximal and distal recesses disposed between the intermediate chamber and the proximal and distal bases, respectively, the mold, having an inner diameter at the proximal and distal bases sufficiently smaller than the inner diameter of the mold at the intermediate chamber, and having an inner diameter at the proximal and distal recesses sufficiently smaller than the inner diameter of the mold at the proximal and distal bases.

4. A mold for forming an inflatable member, comprising:
a generally cylindrical intermediate segment having an intermediate longitudinal dimension and an intermediate interior chamber with an intermediate inner diameter;
proximal and distal segments longitudinally disposed at opposing ends of the intermediate segment and having corresponding interior chambers, the proximal, intermediate, and distal segments being detachable; and
detachable proximal and distal extension shafts configured to connect the proximal and distal segments at their respective proximal and distal ends to a blow-molding machine.

5. The mold of claim 1 further including detachable proximal and distal extension shafts configured to connect the proximal and distal segments at their respective proximal and distal ends to a blow-molding machine.

6. A mold for forming an inflatable member, comprising:
a generally cylindrical intermediate segment having an intermediate longitudinal dimension and an intermediate interior chamber with an intermediate inner diameter;
proximal and distal segments longitudinally disposed at opposing ends of the intermediate segment and having corresponding interior chambers, the proximal, intermediate, and distal segments being detachable, wherein the proximal and distal chambers each has a base at a first end adjacent the intermediate chamber and a second end opposite the first end, the mold having an inner diameter at the proximal and distal bases sufficiently smaller than the inner diameter of the mold at the intermediate segment; and
detachable proximal and distal extension shafts configured to connect the proximal and distal segments at their respective proximal and distal ends to a blow-molding machine.

7. The mold of claim 3 further including detachable proximal and distal extension shafts configured to connect the proximal and distal segments at their respective proximal and distal ends to a blow-molding machine.

8. The mold of claim 4 wherein the segments are formed at least in part from stainless steel.

9. A mold for forming an inflatable member, comprising:
a generally cylindrical intermediate segment having an intermediate interior chamber, said intermediate segment being configured to detachably receive proximal and distal segments;

a plurality of interchangeable proximal segments configured for receipt in said intermediate segment, said plurality of proximal segments being differentiated in terms of interior shape and dimensions; and a plurality of interchangeable distal segments configured for receipt in said intermediate segment, said plurality of distal segments being differentiated in terms of interior shape and dimensions.

10. The mold of claim 9 further including detachable proximal and distal extension shafts configured to connect the proximal and distal segments at their respective proximal and distal ends to a blow-molding machine.

11. The mold of claim 9, wherein the segments are formed at least in part from stainless steel.

* * * * *